(12) United States Patent
Badrena Morales

(10) Patent No.: US 9,788,918 B2
(45) Date of Patent: Oct. 17, 2017

(54) METHOD FOR THE PRODUCTION OF A DENTAL CORRECTION SPLINT AND RESULTING SPLINT

(71) Applicant: Monica Badrena Morales, Barcelona (ES)

(72) Inventor: Monica Badrena Morales, Barcelona (ES)

(73) Assignee: COPRECI, S. COOP, Aretxbaleta (ES)

( * ) Notice: Subject to any disclaimer, the term of this patent is extended or adjusted under 35 U.S.C. 154(b) by 27 days.

(21) Appl. No.: 14/413,185

(22) PCT Filed: Jul. 4, 2013

(86) PCT No.: PCT/ES2013/070469
§ 371 (c)(1),
(2) Date: Apr. 21, 2015

(87) PCT Pub. No.: WO2014/006258
PCT Pub. Date: Jan. 9, 2014

(65) Prior Publication Data
US 2015/0230886 A1    Aug. 20, 2015

(30) Foreign Application Priority Data
Jul. 6, 2012  (ES) .................................. 201231066

(51) Int. Cl.
*A61C 3/00* (2006.01)
*A61C 7/08* (2006.01)
*A61C 5/00* (2017.01)
*G06F 17/50* (2006.01)

(52) U.S. Cl.
CPC ................ *A61C 7/08* (2013.01); *A61C 5/007* (2013.01); *G06F 17/50* (2013.01)

(58) Field of Classification Search
CPC .. A61C 7/08; A61C 7/002; A61C 7/00; A61C 9/004; A61C 9/0046; A61C 5/007; G06F 17/50
USPC .................................. 433/6, 18, 24
See application file for complete search history.

(56) References Cited

U.S. PATENT DOCUMENTS

| | | | | |
|---|---|---|---|---|
| 4,755,139 A * | 7/1988 | Abbatte | ................... | A61C 7/08 433/6 |
| 5,975,893 A * | 11/1999 | Chishti | .................... | A61C 7/00 433/24 |
| 8,936,463 B2 * | 1/2015 | Mason | ................... | A61C 7/002 128/861 |
| 2007/0238065 A1* | 10/2007 | Sherwood | ................ | A61C 7/00 433/24 |

(Continued)

*Primary Examiner* — Matthew Nelson
(74) *Attorney, Agent, or Firm* — Edell, Shapiro & Finnan LLC

(57) ABSTRACT

The invention relates to the production of a dental correction splint (1) and to the resulting splint, in which a patient record is made by taking an impression of his/her teeth (2) and said impression is processed by processing the image of the impression. The method comprises the production of an orthodontic splint (1) which is based on the processed impression and provided externally with the desired result of the correction. The method is characterized in that it includes a step of calculating the internal modifications to the splint (1) by removing and/or replacing the material of the splint (1) which is adapted for each orthodontic movement specific to each stage of the correction.

6 Claims, 1 Drawing Sheet

(56) References Cited

U.S. PATENT DOCUMENTS

2009/0239188 A1* 9/2009 Ting .................. A61C 7/08
433/2

* cited by examiner ns.
METHOD FOR THE PRODUCTION OF A DENTAL CORRECTION SPLINT AND RESULTING SPLINT The object of the present invention is a method for making a splint for dental correction that is aesthetically acceptable, the type that will externally imitate the final result as from the first day of treatment whilst, at an internal level, it will have the capacity of carrying out small orthodontic movements. The final goal is to make the user showing a final simulation of his already aligned teeth from the beginning, and that, internally, said splint modifies the dental arch according the teeth are adapting themselves to their new positions.

BACKGROUND OF THE INVENTION

In dentistry there are known treatments using computer technology in their processes of preparation. In laboratories an image of the whole patient's arch and of the occlusion thereof is obtained by 3D digital scanning from an impression in intra-oral silicone, or even on site from the patient using an intra-oral scanner.

The use this technology helps to develop treatments encompassing almost all dental specialties, as for example in odontology: the Invisalign® system in orthodontic treatments, the Cerec CAD-CAM system in prosthesis, the Nobel Biocare® system in implant surgery, and others.

In summary, most recent advances in technology have changed the way of producing practically all kinds of treatments in odontology. Nowadays, planning and execution of said treatments requires more innovations in software than less complexity in manual processing.

An example of this, is the Snap-on Smile® technique consisting in a technique of cosmetic nature based on the elaboration of a prosthesis of the entire arch that frames the "perfect smile" designed by the dentist based on duly classified standards on a specialized computer support. The dentist takes an impression of the patient's oral cavity either with silicone or by means of intra-oral scanning. Said impression is sent to the laboratory. Thereafter, the dentist elects (in a completely computerized manner) the shape and color being most related to the patient, and the splint is made by means of a Duracetal type polymer.

Finally the lab sends said splint to the dentist, completely made either with all teeth or partially with those framing the "smile" designed by the dentist, so that he may position it on the patient.

This type of prosthesis is essentially cosmetic, with a thickness of some five millimeters, simulating a designed smile with the advantage that the teeth have not been prepared in an irreversible manner.

Another example of said techniques is that known as Invisalign® which is essentially an orthodontic treatment based on a series of practically invisible aligners or splints, which are changed approximately every fifteen days, and the main function of which is to gradually move the teeth with precise and controlled movements. The treatment ends when the final position wished by the dentist has been achieved by means of a program for previewing the treatment's goals.

The impressions of the teeth are scanned to create a digital three-dimensional image with a specific software called ClinCheck® (the function of which is to simulate or preview the goals of the treatment), and movements needed by teeth are analyzed. A simulation of images and virtual representations is made to view the correcting process and how the treatment will be concluded.

The Invisalign® technique uses aligners made of high-molecular weight polyurethane resins, and sends them to the dentist who positions them on the patient (usually a couple of aligners each two weeks) as the treatment is progressing. The process takes approximately between 5-30 months depending on the patient, who will wear said aligners at least 22 hours a day except when ingesting food and/or taking care of his oral hygiene.

In general, no methods and/or systems that combine the characteristics of the different known systems are known

DESCRIPTION OF THE INVENTION

The technical problem solved by the present invention is to obtain a splint with the external structure that simulates the finished orthodontic-esthetic treatment in such a manner that said splint shows the end of the treatment from the beginning, with the advantages inherent in terms of comfort and usability by the user. Until now there did not exist a polymer with a certain flexibility that would allow to be used for orthodontic purposes. Furthermore, the orthodontic movements are internal and do thus not alter the external structure of the final model.

More specifically, in a first aspect of the invention, the method for developing a splint for dental correction which, based on a patient record by taking an impression of his teeth, where said impression will be processed by computer by processing the image of the impression and which comprises making the orthodontic splint based on the computer-processed impression, where it will externally have the potentially expected result of the correction, and which is characterized in that it comprises a step of computing the internal modifications of the split by removing and/or replacing the material of said splint at each orthodontic movement of each correction step.

It should be noted that all steps of the method are performed outside the patient's body, since after the image has been taken, the splint is calculated and modulated externally, so that it will adapt to each stage of the correction.

Years ago, the outcome of an orthodontic treatment, was estimated by tests and gypsum models. Today, with dental software, you can decide what final position you want and what chances a patient does have of having straight teeth. Thus, even patients who for any cause or accident have lost any of their teeth, can show teeth restored while the spaces for future implants or any kind of treatment are being corrected.

In a second aspect of the invention, the splint obtained by the method as described is characterized in that it externally comprises the shape of the potentially expected result, and in that internally it will have a structure which is variable according to the various orthodontic movements required for completing the correction, comprising removal and replacement of material in the splint to perform said orthodontic movements.

Throughout the description and claims, the word "comprise" and its variations are not intended to exclude other technical features, additives, components or steps. To those skilled in the art, other objects, advantages and features of the invention will arise partly from the description and partly from practice of the invention. The following examples and drawings provide by way of illustration, and are not intended to be limiting of the present invention. Furthermore, the present invention covers all possible combinations of particular and preferred embodiments as set forth herein.

BRIEF DESCRIPTION OF THE FIGURES

Hereafter, a series of drawing aiding to a better understanding is described and which are expressly related to an embodiment of said invention presented as a non-limiting example.

PREFERRED EMBODIMENT OF THE INVENTION

Figure 1:
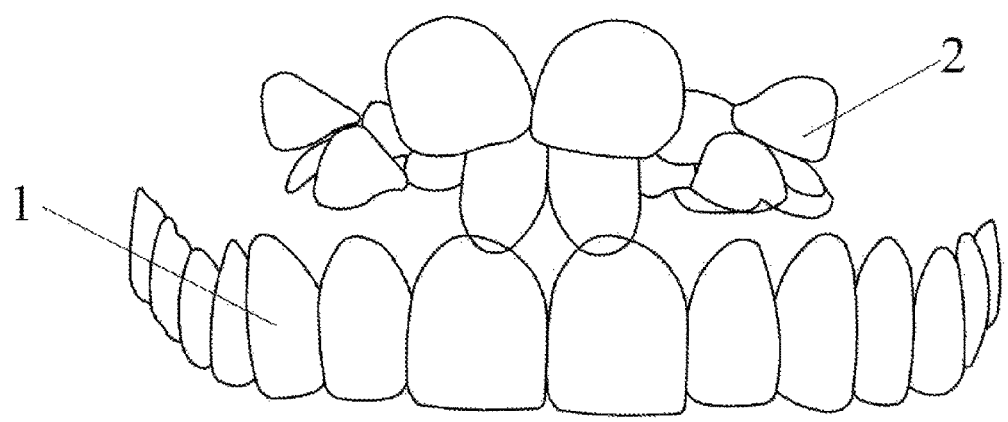
FIG. 1 shows a view of teeth prior to the use of the splint which is the object of the present invention teeth.
Figure 2:
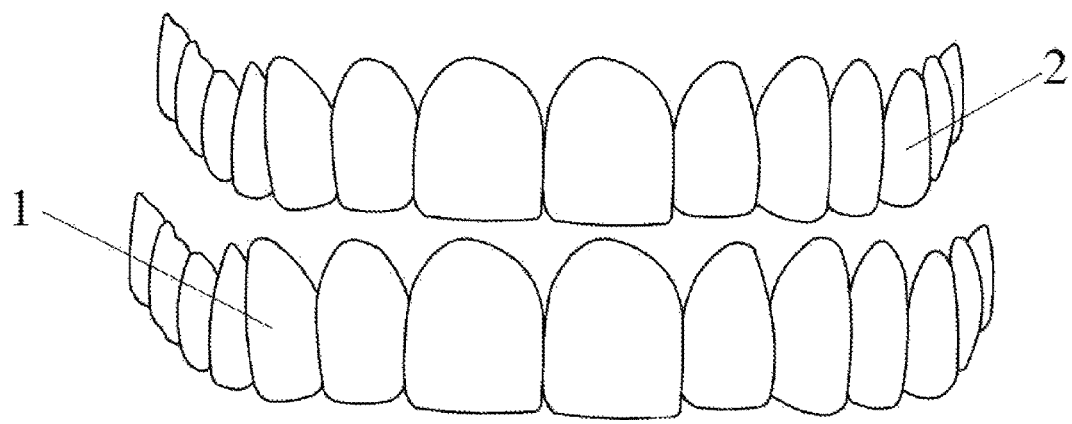
FIG. 2 shows teeth after the splint use which is the object of the present invention has been used.

In a particular embodiment of the invention: the method consists in that firstly a patient a record of the patient is taken either using a silicone impressions or by an intraoral scanner. Thereafter these impressions are sent via modem or inserted in a computer support, for performing the study using software with advanced technology that can simulate said splints by processing the images previously obtained.

All splints will have exactly the same shape, as they will show the potentially expected result (except in those cases where removal is required, where the splint will become externally modified in accordance with the tooth becoming lingualised).

Internally, the splint by subtracting or replacing fitment material, will modify the position making small orthodontic movement. These movements will be achieved with the delivery/successive change of splints.

In this section we may even incorporate into the software alerts to alert us that regarding a certain splint used by the patient, said patient is already prepared to follow some kind of auxiliary or complementary treatment. For example:

Where there is sufficient space for subsequent placement of implants and even perform a double impression so that it serves to us for surgical treatment, performing modifications and extending the splint (1) in a cylinder-like manner in the area of the socket in the future position of the implant, and which will help us in the direction of insertion.

When teeth (2) are in the suitable position to make veneers or vestibular or palatines, either due to an unwanted color or any structural abnormality of the tooth.

To know when a tooth (2), in the case of conoid teeth (teeth with abnormalities in size, microteeth), will be in the lingual lobby to place the restoration mesial-distal and vestibular-lingual position for placing the restoration.

Also at the same splint modifications can be made, such as for example:

Cut lengths at cervical-incisal level when needed, in case subsequent infraocclusion is needed for the placement of an implant.

For esthetic restorations, palatinizing teeth of the anterior sector until obtaining a minimum thickness of 0.3 mm in order to be able to make bridges or crowns when needed.

Splints (1) will be delivered to the patient in accordance with orthodontic movements becoming achieved. Finally, a last treatment retaining splint (1) will be delivered to the patient, or the patient is advised that a conventional retention be performed.

As Stated, the splint (1) obtained has the same external appearance as the finished treatment, while internally its structure is variable depending on the removal and/or replacement of material (silicone) from the inside of the splint (1).

The invention claimed is:

1. A method for preparing a single splint for dental correction requiring a plurality of orthodontic movements achieved in a plurality of steps where the single splint has an internal structure adaptable to an orthodontic movement that is specific to each step of the plurality of steps of the dental correction, the method comprising treating an image of an impression of the teeth of a patient by computer image processing to obtain a computerized image of the impression of the teeth of the patient, processing the computerized image to calculate a potentially expected result of a completed dental correction including final positions of the teeth of the patient, and to calculate steps of dental correction for orthodontic movements required to reach said potentially expected results, receiving the single splint, preparing the single splint adapted to one step of the dental correction by calculating internal modifications of the internal structure of the single splint and modifying the internal structure by at least one of removal and addition of material required to adapt the single splint to enable the orthodontic movement of the teeth to a first intermediate position that is specific to said one step of the dental correction, shaping the splint externally to provide the splint with an external shape having an external structure that simulates the final positions of the teeth of the patient according to the potentially expected result of the completed dental correction, without modifying the external structure of the single splint, preparing the single splint adapted to another step of the dental correction by calculating internal modifications of the internal structure of the single splint and modifying the internal structure by at least one of removal and addition of material required to adapt the single splint to enable the orthodontic movement of the teeth to a second intermediate position that is specific to said another step of the dental correction.

2. The method according to claim 1, further comprising calculating sufficient space for placing subsequent implants.

3. The method according to claim 1, comprising calculating a correct position of the teeth for making palatial vestibular veneers.

4. The method according to claim 1, comprising calculating the mesic-distal and buccolingual position of a conoid teeth for placing a restoration.

5. The method according to claim 1, wherein the internal modifications comprise cutting lengths at cervical-incisival level in cases where subsequent infraocclusion is needed for placing an implant.

6. The method according to claim 1, wherein the modifications of the single splint comprise palatinizing a tooth of an anterior sector until obtaining a minimum thickness of 0.3 mm.

* * * * *

UNITED STATES PATENT AND TRADEMARK OFFICE
CERTIFICATE OF CORRECTION

PATENT NO. : 9,788,918 B2
APPLICATION NO. : 14/413185
DATED : October 17, 2017
INVENTOR(S) : Monica Badrena Morales Page 1 of 1

It is certified that error appears in the above-identified patent and that said Letters Patent is hereby corrected as shown below:

On the Title Page

Cancel the following text in (73) Assignee: section, "COPRECI, S. COOP, Aretxbaleta (ES)"

Signed and Sealed this
Twelfth Day of June, 2018

Andrei Iancu
*Director of the United States Patent and Trademark Office*